(12) United States Patent
Limbach et al.

(10) Patent No.: US 9,969,672 B2
(45) Date of Patent: May 15, 2018

(54) OXIDATIVE ESTERIFICATION PROCESS

(71) Applicant: Rohm and Haas Company, Philadelphia, PA (US)

(72) Inventors: Kirk W. Limbach, Collegeville, PA (US); Dmitri A. Kraptchetov, Collegeville, PA (US); Christopher D. Frick, Collegeville, PA (US)

(73) Assignee: Rohm and Haas Company, Collegeville, PA (US)

( * ) Notice: Subject to any disclaimer, the term of this patent is extended or adjusted under 35 U.S.C. 154(b) by 0 days. days.

(21) Appl. No.: 15/521,750

(22) PCT Filed: Oct. 7, 2015

(86) PCT No.: PCT/US2015/054437
§ 371 (c)(1),
(2) Date: Apr. 25, 2017

(87) PCT Pub. No.: WO2016/069225
PCT Pub. Date: May 6, 2016

(65) Prior Publication Data
US 2017/0226043 A1    Aug. 10, 2017

Related U.S. Application Data

(60) Provisional application No. 62/073,290, filed on Oct. 31, 2014.

(51) Int. Cl.
*C07C 67/00* (2006.01)
*C07C 67/44* (2006.01)

(52) U.S. Cl.
CPC .................................. *C07C 67/44* (2013.01)

(58) Field of Classification Search
CPC ......... C07C 67/39; C07C 67/44; C07C 69/54; B01J 21/04; B01J 21/08; B01J 21/10; B01J 23/44; B01J 23/6445; B01J 23/6447; B01J 35/023; B01J 35/1014
See application file for complete search history.

(56) References Cited

U.S. PATENT DOCUMENTS

| | | |
|---|---|---|
| 4,329,513 A | 5/1982 | Aoshima et al. |
| 4,518,796 A | 5/1985 | Aoshima et al. |
| 5,892,102 A | 4/1999 | Mikami et al. |
| 5,969,178 A | 10/1999 | Okamoto et al. |
| 6,040,472 A * | 3/2000 | Yamamatsu ........... B01J 23/628 502/102 |
| 6,107,515 A | 8/2000 | Yamaguchi et al. |
| 6,228,800 B1 | 5/2001 | Yamaguchi et al. |
| 6,348,619 B1 | 2/2002 | Yoshida et al. |
| RE38,283 E | 10/2003 | Yamamatsu et al. |
| 7,326,806 B2 | 2/2008 | Hayashi et al. |
| 2011/0184206 A1 | 7/2011 | Suzuki et al. |
| 2013/0172599 A1 | 7/2013 | Suzuki et al. |
| 2014/0206897 A1 | 7/2014 | Allman et al. |
| 2016/0068464 A1 | 3/2016 | Krill et al. |

FOREIGN PATENT DOCUMENTS

| | | |
|---|---|---|
| EP | 0972759 A1 | 1/2000 |
| GB | 2094782 A | 9/1982 |
| JP | H10158214 A | 6/1998 |

\* cited by examiner

*Primary Examiner* — Yevgeny Valenrod
*Assistant Examiner* — Blaine G Doletski
(74) *Attorney, Agent, or Firm* — Edward Leonard Brant

(57) ABSTRACT

A process for the preparation of MMA via oxidative esterification in the presence of a catalyst comprising palladium, bismuth, and antimony.

15 Claims, No Drawings

OXIDATIVE ESTERIFICATION PROCESS

BACKGROUND OF THE INVENTION

The invention relates to a process for the preparation of carboxylic acid esters via oxidative esterification.

The production of methyl methacrylate (MMA) from methacrolein (MAL), methanol, and oxygen is known. For example, U.S. Pat. No. 4,518,796 discloses the use of a Pd-bismuth (Bi) catalyst. However, that catalyst did not give high MMA selectivity, which is desired for this reaction.

U.S. Pat. No. 5,892,102 discloses MAL oxidative esterification catalysts that include Pd—Bi—X intermetallics, where X can be a variety of elements, on a ZnO or CaCO$_3$ support. These supports are undesirable from a mechanical stability, likely acid resistance, and long-term catalyst life standpoint.

In view of the deficiencies of the prior art, it would be desirable to have an improved oxidative esterification catalyst for selectively producing MMA.

SUMMARY OF THE INVENTION

The process of the invention is such a process for the preparation of MMA via oxidative esterification, the process comprising contacting MAL, methanol, and an oxygen-containing gas in a reaction zone in the presence of a catalyst comprising palladium, bismuth, and antimony under reaction conditions sufficient to produce MMA.

Surprisingly, the oxidative esterification process of the invention provides a high selectivity to MMA.

DETAILED DESCRIPTION OF THE INVENTION

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc.

Also herein, the recitations of numerical ranges and/or numerical values, including such recitations in the claims, can be read to include the term "about." In such instances the term "about" refers to numerical ranges and/or numerical values that are substantially the same as those recited herein.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

The process of the invention is a process for the preparation of MMA via oxidative esterification, comprising contacting MAL, methanol, and an oxygen-containing gas in the presence of a catalyst comprising palladium, bismuth, and antimony.

Methanol is widely commercially available. MAL can be produced by various industrial scale processes, as known by those skilled in the art. See, e.g., U.S. Pat. Nos. 4,329,513 and 5,969,178.

The ratio of methanol fed to the amount of MAL fed in the reaction of this invention is not particularly limited. The reaction may be conducted over a wide range of methanol to MAL molar ratios, such as 1:10 to 1,000:1, preferably from 1:2 to 50:1, more preferably from 2:1 to 15:1.

The oxygen-containing gas may be either oxygen gas or a mixed gas comprising oxygen gas and a diluent inert to the reaction such as, for example, nitrogen, carbon dioxide or the like. Air may be used as the oxygen-containing gas. The oxygen-containing gas may be enriched air having a higher oxygen concentration than air, or can be pure oxygen. The quantity of oxygen present in the reaction system advantageously is not less than the stoichiometric quantity required for the reaction, and preferably is not less than 1.2 times the stoichiometric quantity. In one embodiment of the invention, the amount of oxygen present in the reaction system is from 1.2 to 2 times the stoichiometric quantity required. Hydrogen peroxide may be introduced into the reaction system as an oxidizer. The oxygen-containing gas can be introduced to the reaction system by an suitable means, as known by those skilled in the art. For example, the oxygen-containing gas can be introduced via a sparger or a pipe into a reactor. The simple method of blowing the oxygen-containing gas into the reaction system can be employed.

The catalyst advantageously is a heterogeneous catalyst comprising a catalytic metal on a porous carrier or support, where the catalytic metal comprises palladium, bismuth, and antimony. Preferably, any catalytic metal is in the reduced state, namely zero valency, and not in the cationic state, and may be present in the reduced state or as one or more compounds. The catalytic metals are present in the reaction system in such a form that they can have some interaction with each other. For example, palladium, bismuth and antimony may form an alloy, or have some other interaction, such as an intermetallic compound. In one embodiment of the invention, the catalyst may comprise a palladium intermetallic compound in which the lattice of palladium has been replaced with a diverse metal, e.g., bismuth or antimony. In another embodiment of the invention, the catalyst may comprise a palladium alloy in which palladium and a diverse metal have formed a solid solution. The ratio of palladium to bismuth in the catalyst is preferably 20:1 to 1:10 (weight ratio), and more preferably is from 5:1 to 1:1. The ratio of Sb to bismuth is advantageously from 100:1 to 1:10 (weight ratio), and in various embodiments of the invention is from 1:1 to 1:4. In one embodiment of the invention, the catalyst and/or the catalytic metal is free of added lead.

The catalytic metals may be supported on a carrier or support, such as activated carbon, magnesium oxide, zinc oxide, titanium oxide, calcium carbonate, silica or alumina, and the amount of the catalytic constituents supported on the carrier advantageously may be from 0.1 to 20% by weight, preferably 1 to 10% by weight, based on the weight of the carrier. In one embodiment of the invention, the carrier comprises at least one of silica, alumina, and silica-alumina.

Examples of carriers include silica gel, precipitated silica, fumed silica, spray dried colloidal silica, silica doped with alumina (also referred to herein as silica-alumina) or other materials, delta alumina, theta alumina, alumina doped with silica (also referred to herein as alumina-silica) or other materials, and gamma alumina. The carrier may be modified, as is known by those skilled in the art. For example, a silica carrier may be modified with one or more additional materials such as, for example, alumina and/or magnesia. Combinations of carriers may be employed. The catalyst constituents may also be used in the metallic form or in the form of compounds without supporting them on a carrier. In one embodiment of the invention, the catalyst is homogeneous.

The catalyst can be prepared in a conventional manner. For example, a soluble salt, such as palladium chloride, can be reduced with a reducing agent, such as formalin, in aqueous solution to deposit metallic palladium and the deposited metallic palladium can be filtered to prepare a metallic palladium catalyst, or a suitable carrier can be impregnated with an aqueous acidic solution of a soluble palladium salt and the impregnated carrier subjected to reduction with a reducing agent to prepare a supported palladium catalyst. In one embodiment of the invention, when it is intended to prepare a catalyst in which palladium, bismuth and antimony, are supported on a carrier, a suitable carrier is impregnated with an aqueous solution of a soluble palladium salt, and the impregnated carrier is reduced with a suitable reducing agent, after which the reduced carrier is immersed in an aqueous solution of a bismuth compound and a compound of antimony, and then dried. Alternatively, the catalyst may be prepared by first supporting the bismuth compound on the carrier, then impregnating the carrier with palladium and at least one antimony compound, and thereafter adding a reducing agent, such as hydrazine. In one embodiment of the invention, the 3 catalytic metal compounds are all introduced prior to reduction. Thus, the metals can be added in any sequence and in any combination appropriate to produce a workable catalyst. Other examples of reducing agents include formic acid, methanol, hydrogen gas and the like.

As the bismuth compound used in the preparation of the above catalyst, any suitable bismuth-containing compound may be used. For example, fatty acid salts of bismuth, such as bismuth acetate, bismuth stearate, and the like can be employed. Other suitable compounds include bismuth oxide; bismuth hydroxide; and bismuth nitrate. These bismuth compounds may be anhydrous or may be in the form of a hydrate. As the antimony compound used in the preparation of the above catalyst, any suitable antimony-containing compound may be used. Examples of antimony-containing compounds include antimony acetate, antimony chloride, antimony nitrate, and antimony sulfate. These antimony compounds may be anhydrous or may be in the form of a hydrate.

As the palladium compound used in the preparation of the catalyst, any suitable palladium-containing compound may be used. For example, fatty acid salts of palladium, such as palladium acetate, palladium stearate, and the like can be employed. Other suitable compounds include palladium oxide; palladium hydroxide; and palladium nitrate. These palladium compounds may be anhydrous or may be in the form of a hydrate.

The surface area of the catalyst advantageously is sufficient to allow the reaction to proceed. In various embodiments of the invention, the surface area of the catalyst is at least 50 m$^2$/g, at least 60 m$^2$/g, at least 70 m$^2$/g, or at least 100 m$^2$/g. These surface areas are as measured by the Brunauer-Emmett-Teller (BET) method. The BET method is described by R. B. Anderson, *Experimental Methods in Catalytic Research*, pp. 48-66, Academic Press (1968). In various embodiments of the invention, the surface area of the catalyst is not more than 400 m$^2$/g, not more than 350 m$^2$/g, or not more than 300 m$^2$/g.

The median particle size of the catalyst, particularly when the catalyst will be used in a slurry, advantageously is from 1 to 200 microns, preferably is from 3 to 120 microns, and more preferably 5 to 100 microns. The median particle size is volume based, and is a $D_{50}$ size in microns that splits the particle size distribution, with half the observed volume above, and half below, that diameter. In various embodiments of the invention, when the catalyst will be used in a fixed bed, the median particle size advantageously will be larger such as, for example, from 1 to 10 mm.

It is possible to employ as the catalyst an article that has a supported catalytic metal layer in a specific shallow region in the vicinity of the outer surface of the carrier and that further has a layer on the outer surface of the carrier that is substantially free of catalytic metal. Catalysts of this type are described in U.S. Pat. No. 6,228,800, the teachings of which are incorporated herein by reference. The catalyst can also have the catalytic metal distributed evenly on the surface of the carrier or can have the catalytic metal distributed evenly or homogeneously throughout the carrier.

The catalyst may be subjected to activation and/or regeneration, as is known to those skilled in the art. For example, U.S. Pat. No. 6,040,472 discloses various catalyst activation techniques.

The catalyst is employed in a catalytic amount. The amount of the catalyst, i.e., catalytic metals and optional carrier, may be varied freely depending on the kind and amount of the starting materials, the method of preparing the catalyst, composition of the catalyst, process operating conditions, reactor type, and the like, although the weight ratio of catalyst to the starting aldehyde generally is from 1:1000 to 20:1. Advantageously, the ratio of catalyst to aldehyde is from 1:100 to 4:1. However, the catalyst may be used in an amount outside these ranges.

The process for producing MMA comprises contacting reactants comprising MAL, methanol and an oxygen-containing gas, under oxidative esterification conditions in the presence of the catalyst. Oxidative esterification conditions include, for example, the oxygen partial pressure, reaction total pressure, temperature, concentration of reactants, pH and reaction time suitable to produce the desired reaction product. In one embodiment of the invention, the reaction may be conducted using a slurry of the catalyst in the liquid phase in the reaction zone. The reaction may be conducted at a temperature of from 0° C. to 120° C., preferably from 40° C. to 90° C. The reaction may be conducted at reduced pressure, at atmospheric pressure, or at superatmospheric pressure. The reaction pressure for oxidative esterification reactions is advantageously selected within a range at which the catalyst is active for oxidative esterification reactions. The reaction may be conducted at a pressure of from 50 to 2000 kPa (7.3 to 290 psia), preferably from 100 to 1000 kPa (14.5 to 145 psia). The reaction may be conducted in a batch, semi-batch or continuous manner.

The reaction may be conducted in any suitable reactor type such as, for example, a CSTR, a bubble column reactor or a fixed bed reactor. The reactor can be stirred or not stirred, and may have a mobile catalyst that generally moves with the reaction liquid, or may contain a fixed bed of catalyst through which the reaction fluid flows. Recycling of reaction fluids through the reactor can be conducted in any of these configurations. In an embodiment, a single reactor with a single reaction zone is used.

In one embodiment of the invention, the reaction is carried out in the slurry phase. The catalyst may then be separated from the product mixture, for example, by filtration or decantation. In various embodiments of the invention, the "reaction fluid," which may be a mixed phase composition comprising solids, liquids and gases, may contain a heterogeneous catalyst, e.g., slurry, or at least a portion of the reaction fluid may contact a fixed bed of catalyst during the process.

In an embodiment, the oxygen partial pressure varies depending on the reactants, reaction conditions and type of reactor. In an embodiment, the oxygen partial pressure on the outlet side of the reactor is a positive pressure of less than or equal to 35 kPa (5 psia). In an embodiment, the oxygen partial pressure on the outlet side of the reactor is a positive pressure of less than or equal to 200 kPa (29 psia).

In an embodiment, the pH of the reaction is maintained in the range of 6 to 9. If necessary to maintain the pH, an alkaline material, such as an alkali metal compound or alkaline earth metal compound, may be added to the reaction. Exemplary alkaline materials include alkali metal and alkaline earth metal compounds that include, but are not limited to, oxides, hydroxides, carbonates, and carboxylic acid salts.

The reaction time varies depending on the reaction conditions, reactants and other factors which may influence the reaction. Typically, however, the reaction time is from 0.5 to 20 hours. For a continuous process, such as in embodiments using a continuous stirred tank reactor CSTR, the reaction time (residence time) is governed by the kinetics of the system as determined by the pressure, temperature and catalyst used.

In an embodiment, the process includes removing a crude product stream from the reactor. The crude product stream comprises MMA along with unreacted methanol, MAL and oxygen, as well as various amounts of by-products such as, for example, water, methacrylic acid, methyl formate and other by-products.

A polymerization inhibitor can be employed in the process when the product is a polymerizable compound. A wide variety of inhibitors are known and commercially available. Examples of inhibitors include hydroquinone (HQ), phenothiazine (PTZ), the methyl ester of hydroquinone (MEHQ), 4-hydroxy-2 2 6 6-tetramethylpiperidine-n-oxyl (4-hydroxy TEMPO, or 4HT), methylene blue, alkyl-aryl-phenylenediamine, copper salicylate, copper dialkyldithiocarbamates, and the like.

In various embodiments of the invention, the catalyst is employed in said esterification to provide a selectivity to MMA of at least 90%, or at least 95%, or at least 98%, or at least 99%, based on MAL. For the purposes of the invention, yield is calculated as the mathematical product of conversion times selectivity.

SPECIFIC EMBODIMENTS OF THE INVENTION

The following examples are given to illustrate the invention and should not be construed as limiting its scope.

Calculation of Conversion and Selectivity:

Conversion and selectivity are calculated ignoring a 5 hour catalyst activation period. The concentration of various constituents is obtained at the fifth hour of operation and the twenty-second hour of operation. Condensate from the dry ice condenser is returned to the reactor, and the samples are dilute in nature. Organic vapor losses and changes to sample weights are assumed to be minimal. The reactor contents are analyzed via a gas chromatograph (GC) with a flame ionization detector (FID).

MAL conversion is calculated as the moles of MAL reacted during the relevant time period (i.e., the moles of MAL present at the fifth hour minus the moles of MAL present at the twenty second hour) divided by the moles of MAL present at the fifth hour, and is expressed as a percentage.

Selectivity to MMA is calculated as the moles of MMA made (from hour five to hour twenty two) divided by the moles of MAL consumed over that time period, and is also expressed as a percentage.

Example 1

Catalyst Preparation: A catalyst having 5 wt % Pd, 2 wt % Bi, and 1 wt % Sb on an alumina carrier is prepared using Sigma Aldrich 5 wt % Pd on alumina as a starting point. A slurry is prepared by dissolving 0.90 grams of bismuth nitrate pentahydrate in 100 ml of deionized water, then adding 0.47 g antimony acetate to provide 1 wt % Sb on a carrier basis, and then adding 20.0 grams of the Aldrich Pd/alumina. The slurry is stirred for 1 hour at 60° C., then 10.0 grams of hydrazine hydrate are added slowly, dropwise, and the resulting mixture is stirred for an additional 1 hour at 90° C. The resulting solids are then separated via vacuum filtration, are washed with 500 ml of deionized water, and are vacuum dried at 45° C. for 10 hours.

MMA Preparation: A 5 gram sample of the catalyst is placed in a 300 ml glass reactor with a 100 g solution of 4.0 wt % MAL in methanol. The glass reactor is fitted with a pitched-blade turbine impeller, dry ice condenser and dry ice traps. The reactor is maintained at 40° C. by immersion in a constant temperature bath and is operated at atmospheric pressure. The reactor is run in a semi-batch mode having a batch liquid phase organic reactant and catalyst slurry that is continuously sparged by 8% $O_2$ in $N_2$ gas. The gas flows continuously into the liquid through a fine glass frit which generates small bubbles. The bubbles and the catalyst are well distributed throughout the liquid due to agitation induced by the impeller. The solution also contains, as a polymerization inhibitor, approximately 50 ppm 4-HT in combination with PTZ (approximately 10 ppm) and HQ (approximately 10 ppm). The reactor is operated in this manner for a total of approximately 22 hours and samples are obtained at the beginning of the experiment, at the fifth hour of the experiment, and at the end of the experiment.

Conversion of MAL is 100%. Selectivity to MMA is approximately 86% based on MAL. The yield is calculated as 1×0.86=86%.

Example 2

Example 1 is repeated except that the solution of MAL in methanol contains 4.7 wt % MAL.

Conversion of MAL is 92%. Selectivity to MMA is above 99% based on MAL. The yield is calculated as 0.92× 0.99=91%.

Example 3

Catalyst Preparation: A catalyst having 5 wt % Pd, 2 wt % Bi, and 1 wt % Sb on a gamma alumina carrier is prepared using 5 wt % Pd and 2 wt % Bi on alumina as a starting point. The carrier is T-2610 micro-spherical gamma alumina from Clariant, having a median particle size of from 55 to 80 microns and a surface area of from 120 to 150 m²/g. This catalyst is made by first using incipient wetness impregnation of the nitrate salt of Pd followed by calcining in air at atmospheric pressure and for sufficient time to denitrify the material. Bi is then added to the material by incipient wetness impregnation of the nitrate salt of Bi followed by calcining in air at atmospheric pressure for sufficient time to denitrify that material. A slurry is prepared by dissolving 0.47 g antimony acetate to provide 1 wt % Sb on a carrier basis, and then adding 20.0 grams of the Pd/Bi material. The slurry is stirred for 1 hour at 60° C., after which 10.0 grams of hydrazine hydrate are added slowly, dropwise, and stirred for an additional 1 hour at 90° C. The resulting solids are then separated via vacuum filtration, are washed with 500 ml of deionized water, and are vacuum dried at 45° C. for 10 hours.

MMA Preparation: A 5 gram sample of the catalyst is placed in a glass reactor with a 100 g solution of 4.4 wt % MAL in methanol. The solution also contains, as polymerization inhibitor, approximately 50 ppm 4-HT in combination with PTZ (approximately 10 ppm) and HQ (approximately 10 ppm).

Conversion of MAL is 100%. Selectivity to MMA is approximately 82% based on MAL. The yield is calculated as 1×0.82=82%.

Example 4

MMA Preparation: Example 3 is repeated except that the solution of MAL in methanol contains 4.5 wt % MAL.

Conversion of MAL is 100%. Selectivity to MMA is approximately 93% based on MAL. The yield is calculated as 1×0.93=93%.

Example 5

Catalyst Preparation: A catalyst having 5 wt % Pd, 2 wt % Bi, and 1 wt % Sb on a silica-alumina carrier is prepared using 5 wt % Pd and 2 wt % Bi on silica-alumina as a starting point. The carrier is T-2865 micro-spherical silica-modified gamma alumina from Clariant, having a median particle size of from 55 to 80 microns and a surface area of from 120 to 150 m²/g. This catalyst is made by first using incipient wetness impregnation of the nitrate salt of Pd followed by calcining in air at atmospheric pressure and for sufficient time to denitrify the material. Bi is then added to the material by incipient wetness impregnation of the nitrate salt of Bi followed by calcining in air at atmospheric pressure for sufficient time to denitrify that material. A slurry is prepared by dissolving 0.47 g antimony acetate to provide 1 wt % Sb on a carrier basis, and then adding 20.0 grams of the Pd/Bi material. The slurry is stirred for 1 hour at 60° C., after which 10.0 grams of hydrazine hydrate are added slowly, dropwise, and stirred for an additional 1 hour at 90° C. The resulting solids are then separated via vacuum filtration, are washed with 500 ml of deionized water, and are vacuum dried at 45° C. for 10 hours.

MMA Preparation: Example 3 is repeated except that the solution of MAL in methanol contains 4.4 wt % MAL.

Conversion of MAL is 100%. Selectivity to MMA is above 99% based on MAL. The yield is above 99%.

Example 6

MMA Preparation: Example 5 is repeated.

Conversion of MAL is 100%. Selectivity to MMA is above 99% based on MAL. The yield is above 99%.

What is claimed is:

1. A process for the preparation of methyl methacrylate (MMA) via oxidative esterification, the process comprising contacting methacrolein, methanol, and an oxygen-containing gas in a reaction zone in the presence of a catalyst comprising palladium, bismuth, and antimony under reaction conditions sufficient to produce MMA.

2. The process of claim 1 wherein the catalyst is a heterogeneous catalyst comprising a catalytic metal on a porous carrier or support, where the catalytic metal comprises palladium, bismuth, and antimony.

3. The process of any of claim 1 wherein the weight ratio of palladium to bismuth in the catalyst is from 20:1 to 1:10.

4. The process of claim 1 wherein the weight ratio of Sb to bismuth is from 100:1 to 1:10.

5. The process of claim 1 wherein the catalyst is a supported catalyst and the support comprises at least one of activated carbon, magnesium oxide, zinc oxide, titanium oxide, calcium carbonate, silica-alumina, alumina-silica, silica or alumina.

6. The process of claim 1 wherein the catalyst is a supported catalyst and the amount of the catalytic metal on the support is from 0.1 to 20% by weight, based on the weight of the support.

7. The process of claim 1 wherein the catalyst is a supported catalyst and the surface area of the catalyst is at least 50 m²/g.

8. The process of claim 1 wherein the catalyst is a supported catalyst and the median particle size of the supported catalyst is from 1 to 200 microns.

9. The process of claim 1 wherein the catalyst is a supported catalyst and the support comprises at least one of alumina and silica.

10. The process of claim 1 wherein the catalyst is a supported catalyst and the support comprises silica modified with magnesia.

11. The process of claim 1 wherein the catalyst is a supported catalyst and the support comprises primarily silica.

12. The process of claim 1 wherein the catalyst is a supported catalyst and the support is modified with alumina, magnesia, or a combination thereof.

13. The process of claim 1 wherein the weight ratio of palladium to bismuth in the catalyst is from 5:1 to 1:1, and the weight ratio of Sb to bismuth is from 1:1 to 1:4.

14. The process of claim 1 wherein the weight ratio of the catalyst in the reaction zone to methacrolein fed to the reaction zone is from 1:1000 to 20:1.

15. The process of claim 1 wherein the temperature in the reaction zone is from 0° C. to 120° C., and the pressure in the reaction zone is from 50 to 2000 kPa (7.3 to 290 psia).

* * * * *